United States Patent [19]

Rodriguez

[11] Patent Number: 5,629,289
[45] Date of Patent: May 13, 1997

[54] CYCLIC PEPTIDE ANTIFUNGAL AGENTS

[75] Inventor: Michael J. Rodriguez, Indianapolis, Ind.

[73] Assignee: Eli Lilly and Company, Indianapolis, Ind.

[21] Appl. No.: 506,790

[22] Filed: Jul. 25, 1995

[51] Int. Cl.$^6$ .................................................. A61K 38/12
[52] U.S. Cl. ............................. 514/11; 514/9; 530/317; 530/318
[58] Field of Search ..................... 514/11, 9; 530/317, 530/318

[56] References Cited

U.S. PATENT DOCUMENTS

| | | | |
|---|---|---|---|
| 5,057,493 | 10/1991 | Takesako et al. | 514/11 |
| 5,059,540 | 10/1991 | Bailey | 436/89 |
| 5,158,876 | 10/1992 | Takesako et al. | 435/71.1 |
| 5,166,135 | 11/1992 | Schmatz | 514/11 |
| 5,200,505 | 4/1993 | Takesako et al. | 530/323 |
| 5,260,214 | 11/1993 | Takesako et al. | 435/254.1 |
| 5,376,634 | 12/1994 | Iwamoto et al. | 514/9 |

FOREIGN PATENT DOCUMENTS

| | | |
|---|---|---|
| 0352092 | 7/1989 | European Pat. Off. . |
| 0443719 | 1/1991 | European Pat. Off. . |
| 0510271 | 4/1991 | European Pat. Off. . |
| 0581429 | 6/1993 | European Pat. Off. . |
| 94/25045 | 4/1994 | WIPO . |

OTHER PUBLICATIONS

*J. Org. Chem.*, 1981, 46, 4789–4791.

*J. Antibiotics*, Sep. 1991, vol. 44, No. 9, 925–933.

*J. Antibiotics*, Sep. 1991, vol. 44, No. 9, 919–924.

*J. Molecular Structure* (Theochem), 180 (1988) 383–387.

U.S. application Ser. No. 08/339,525, Filing Date Nov. 15, 1994.

*Primary Examiner*—Cecilia Tsang
*Assistant Examiner*—Anish Gupta
*Attorney, Agent, or Firm*—Janet T. McClain; David E. Boone

[57] ABSTRACT

Provided are pharmaceutical formulations, and methods of inhibiting fungal and parasitic activity using a compound of formula I:

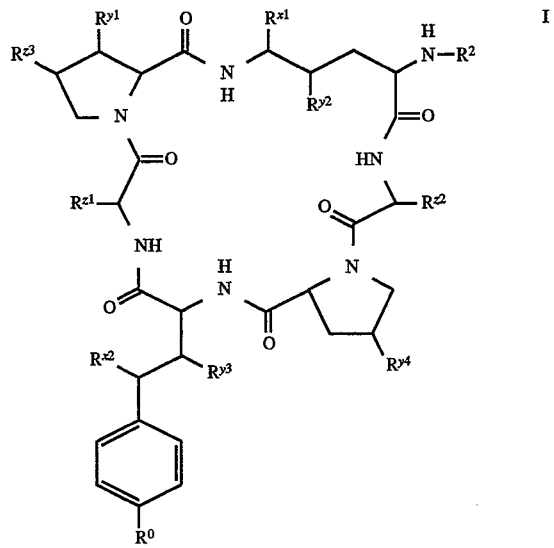

wherein:

$R^{z1}$ is hydrogen, —$CH_2OH$, —$CHOHCH_3$ or —$CHOHCH_2C(O)NH_2$;

$R^{z2}$ is hydrogen, —$CH_2OH$ or —$CHOHCH_3$;

$R^{z3}$ is hydrogen or methyl;

$R^{x1}$ is hydrogen, hydroxy or O—$R^{x1'}$;

$R^{x1'}$ is $C_1$–$C_6$ alkyl, benzyl, —$(CH_2)_2Si(CH_3)_3$, —$CH_2CH$=$CH_2$, —$CH_2CHOHCH_2OH$, —$(CH_2)_aCOOH$, —$(CH_2)_bNR^{w1}R^{w2}$, —$(CH_2)_cPOR^{w3}R^{w4}$ or —$[(CH_2)_2O]_d$—$(C_1$–$C_6)$alkyl;

a, b and c are independently 1, 2, 3, 4, 5 or 6;

$R^{w1}$ and $R^{w2}$ are independently hydrogen, $C_1$–$C_6$ alkyl, or $R^{w1}$ and $R^{w2}$ combine to form —$CH_2(CH_2)_eCH_2$—;

$R^{w3}$ and $R^{w4}$ are independently hydroxy, or $C_1$–$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —$OP(O)(OH)_2$ or a group of the formulae:

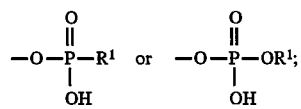

$R^1$ is $C_1$–$C_6$ alkyl, phenyl, p-halo-phenyl, p-nitrophenyl, benzyl, p-halo-benzyl or p-nitro-benzyl;

$R^2$ is $R^3$ is

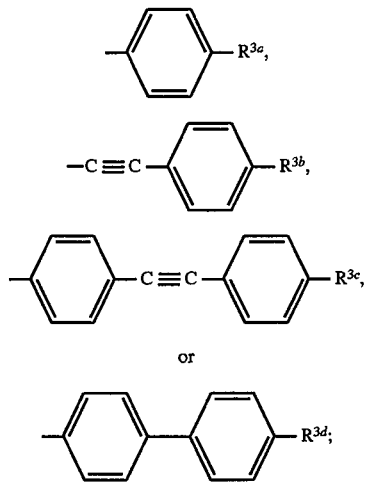

$R^{3a}$, $R^{3b}$, $R^{3c}$ and $R^{3d}$ are independently hydrogen, $C_1$–$C_{12}$ alkyl, $C_2$–$C_{12}$ alkynyl, $C_1$–$C_{12}$ alkoxy, $C_1$–$C_{12}$ alkylthio, halo, —O—$(CH_2)_m$—[O—$(CH_2)_n]_p$—O—($C_1$–$C_{12}$ alkyl) or —O—$(CH_2)_q$—X—$R^4$;

m is 2, 3 or 4;

n is 2, 3 or 4;

p is 0 or 1;

q is 2, 3 or 4;

X is pyrrolidino, piperidino or piperazino; and $R^4$ is hydrogen, $C_1$–$C_{12}$ alkyl, $C_3$–$C_{12}$ cycloalkyl, benzyl or $C_3$–$C_{12}$ cycloalkylmethyl;

with the proviso that at least one of $R^{z1}$ and $R^{z2}$ must be hydrogen;

or a pharmaceutically acceptable salt thereof.

24 Claims, No Drawings

CYCLIC PEPTIDE ANTIFUNGAL AGENTS

BACKGROUND OF THE INVENTION

This invention relates to semi-synthetic cyclic peptide compounds which are useful as antifungal agents and which have improved stability and water solubility. In particular, it relates to derivatives of the echinocandin class of cyclic peptides; to methods for treating fungal infections, and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R^2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula I where $R^{z1}$ and $R^{z2}$ are each —CHOHCH$_3$, $R^{z3}$ is methyl; $R^{x1}$ is hydrogen, $R^{x2}$, $R^{y1}$, $R^{y2}$, $R^{y3}$, $R^{y4}$ and $R^0$ is hydroxy and $R_2$ is p-(octyloxy)benzoyl.

SUMMARY OF THE INVENTION

The present invention provides a compound of formula I:

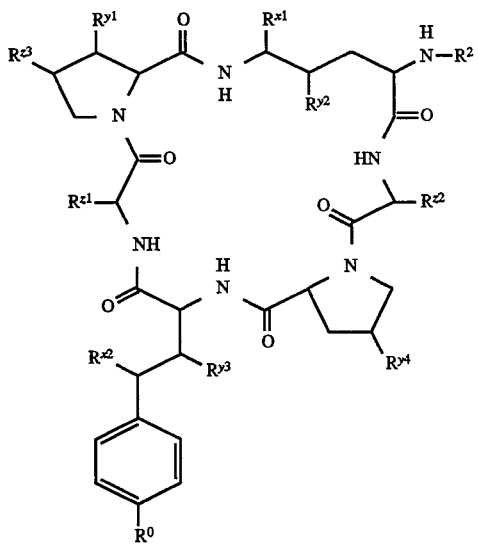

wherein:

$R^{z1}$ is hydrogen, —CH$_2$OH, —CHOHCH$_3$ or —CHOHCH$_2$C(O)NH$_2$;

$R^{z2}$ is hydrogen, —CH$_2$OH or —CHOHCH$_3$;

$R^{z3}$ is hydrogen or methyl;

$R^{x1}$ is hydrogen, hydroxy or O—$R^{x1'}$;

$R^{x1'}$ is $C_{1-C_6}$ alkyl, benzyl, —(CH$_2$)$_2$Si(CH$_3$)$_3$, —CH$_2$CH=CH$_2$, —CH$_2$CHOHCH$_2$OH, —(CH$_2$)$_a$COOH, —(CH$_2$)$_b$NR$^{w1}$R$^{w2}$, —(CH$_2$)$_c$POR$^{w3}$R$^{w4}$ or —[(CH$_2$)$_2$O]$_d$—(C$_1$–C$_6$)alkyl;

a, b and c are independently 1, 2, 3, 4, 5 or 6;

$R^{w1}$ and $R^{w2}$ are independently hydrogen, C$_1$-C$_6$ alkyl, or $R^{w1}$ and $R^{w2}$ combine to form —CH$_2$(CH$_2$)$_e$CH$_2$—;

$R^{w3}$ and $R^{w4}$ are independently hydroxy, or C$_1$–C$_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —OP(O)(OH)$_2$ or a group of the formulae:

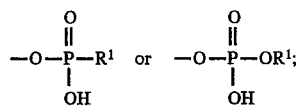

$R^1$ is C$_1$–C$_6$ alkyl, phenyl, p-halo-phenyl, p-nitrophenyl, benzyl, p-halo-benzyl or p-nitro-benzyl;

$R^2$ is

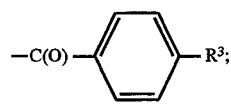

$R^3$ is

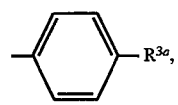

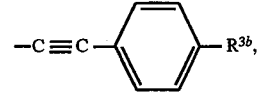

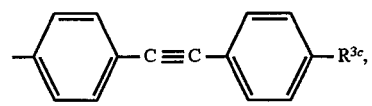

or

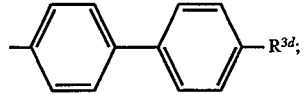

$R^{3a}$, $R^{3b}$, $R^{3c}$ and $R^{3d}$ are independently hydrogen, C$_1$–C$_{12}$ alkyl, C$_2$–C$_{12}$ alkynyl, C$_1$–C$_{12}$ alkoxy, C$_1$–C$_{12}$ alkylthio, halo, —O—(CH$_2$)$_m$—[O—(CH$_2$)$_n$]$_p$—O—(C$_1$–C$_{12}$ alkyl) or —O—(CH$_2$)$_q$—X—R$^4$;

m is 2, 3 or 4;

n is 2, 3 or 4;

p is 0 or 1;

q is 2, 3 or 4;

X is pyrrolidino, piperidino or piperazino; and $R^4$ is hydrogen, C$_1$–C$_{12}$ alkyl, C$_3$–C$_{12}$ cycloalkyl, benzyl or C$_3$–C$_{12}$ cycloalkylmethyl; with the proviso that at least one of $R^{z1}$ and $R^{z2}$ must be hydrogen;

or a pharmaceutically acceptable salt thereof.

Also provided are pharmaceutical formulations, methods for inhibiting fungal activity and methods of treating fungal infections which employ the compounds of the invention.

DETAILED DESCRIPTION OF THE INVENTION

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1$–$C_{12}$ alkyl" includes within its definition the term "$C_1$–$C_6$ alkyl."

The term "halo" refers to chloro, fluoro, bromo or iodo.

The term "$C_2$–$C_{12}$ alkynyl" refers to a straight or branched alkynyl chain having from two to twelve carbon atoms. Typical $C_2$–$C_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "$C_1$–$C_{12}$ alkylthio" refers to a straight or branched alkyl chain having from one to twelve carbon atoms attached to a sulfur atom. Typical $C_1$–$C_{12}$ alkylthio groups include methylthio, ethylthio, propylthio, isopropylthio, butylthio, 3-methyl-heptylthio, octylthio, 5,5-dimethylhexylthio and the like.

The term "$C_1$–$C_{12}$ alkoxy" refers to a straight or branched alkyl chain having from one to twelve carbon atoms attached to an oxygen atom. Typical $C_1$–$C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1$–$C_{12}$ alkyl" includes within its definition the term "$C_1$–$C_6$ alkoxy."

The term "$C_3$–$C_{12}$ cycloalkyl" refers to a saturated hydrocarbon ring structure having from three to twelve carbon atoms. Typical $C_3$–$C_{12}$ cycloalkyl groups include cyclopropyl, cyclobutyl, cyclopentyl, cyclohexyl and cycloheptyl, cyclooctyl and the like. The term "$C_3$–$C_{12}$ cycloalkylmethyl" refers to a $C_3$–$C_{12}$ cycloalkyl attached to a methylene group.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, trimethylsilylethyl, (t-butyl)dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilylethyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy protecting groups.

The term "inhibiting", i.e. a method of inhibiting fungal activity, includes stopping, retarding or prophylactically hindering or preventing the growth or any attending characteristics and results from the existence of a fungus.

The term "contacting", i.e. contacting a compound of the invention with a fungus, includes a union or junction, or apparent touching or mutual tangency of a compound of the invention with a fungus. However, the term does not imply any further limitations to the process, such as by mechanism of inhibition, and the methods are defined to encompass the spirit of the invention, which is to inhibit fungal activity by the action of the compounds and their inherent antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

$R^{z1}$ is hydrogen, —CH$_2$OH or —CHOHCH$_3$; or a pharmaceutically acceptable salt thereof.

Of these compounds, more preferred are those compounds of formula I where:

$R^{z1}$ and $R^{z2}$ are independently hydrogen or —CHOHCH$_3$;
$R^{z3}$ is methyl;
$R^{y1}$, $R^{y2}$, $R^{y3}$ and $R^{y4}$ are each hydroxy;
$R^{x1}$ is hydrogen, hydroxy or —OR$^{x1'}$;
$R^{x1'}$ is methyl, benzyl, —CH$_2$CHOHCH$_2$OH, —CH$_2$COOH, —(CH$_2$)$_2$NR$^{w1}$R$^{w2}$ or —(CH$_2$)$_2$POR$^{w3}$R$^{w4}$;
$R^{w1}$ and $R^{w2}$ are independently hydrogen or methyl;
$R^{w3}$ and $R^{w4}$ are independently hydrogen or methoxy;
$R^{o}$ is hydroxy or a group of the formulae:

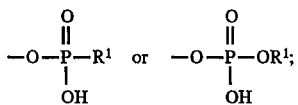

$R^1$ is methyl;
or a pharmaceutically acceptable salt thereof.

Of these preferred compounds, further preferred are those compounds of formula I where:
$R^{z1}$ and $R^{z2}$ are both hydrogen;
$R^{x1}$ is hydrogen;
$R^{x2}$ is hydrogen;

$R^3$ is

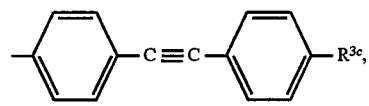

or

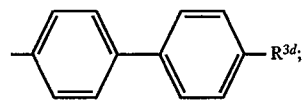

$R^{3c}$ and $R^{3d}$ are independently hydrogen, C$_1$–C$_{12}$ alkyl, C$_2$–C$_{12}$ alkynyl, C$_1$–C$_{12}$ alkoxy or —O—(CH$_2$)$_2$-O-(C$_1$—C$_{12}$ alkyl);

or a pharmaceutically acceptable salt thereof.

Of these compounds the most preferred compounds are those compounds where:

$R^3$ is

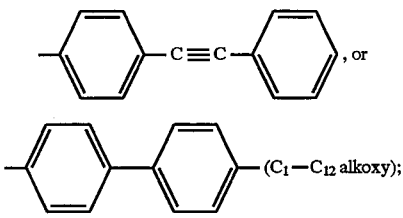

or a pharmaceutically acceptable salt thereof.

The compounds of formula I may be prepared according to Reaction Scheme I, as follows.

Reaction Scheme I

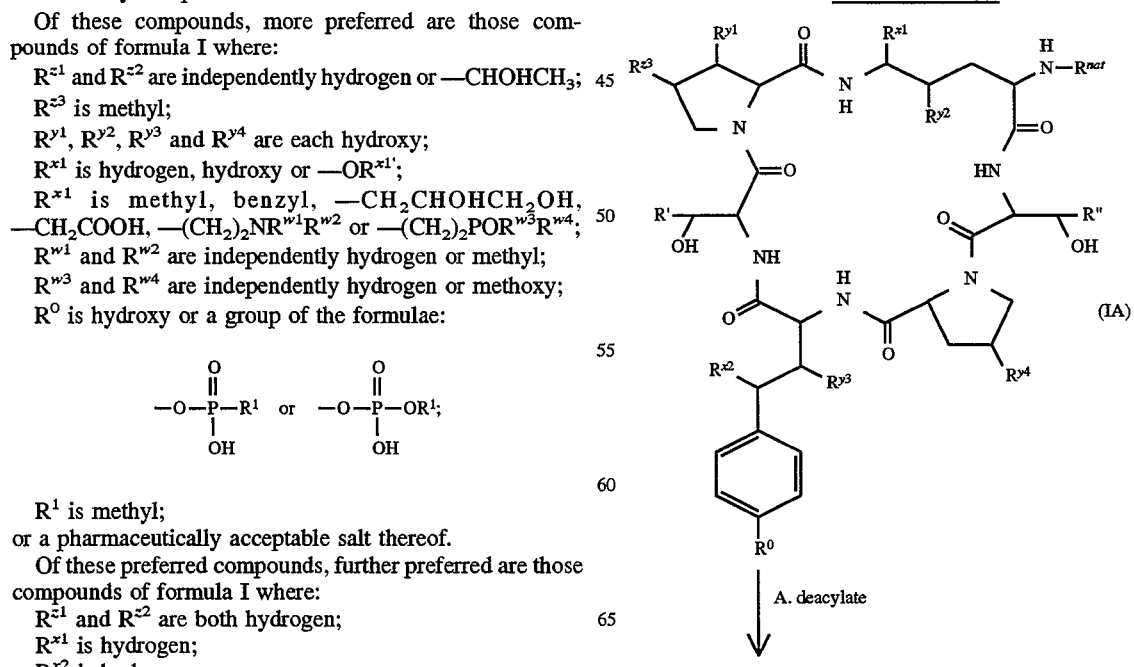

-continued
Reaction Scheme I

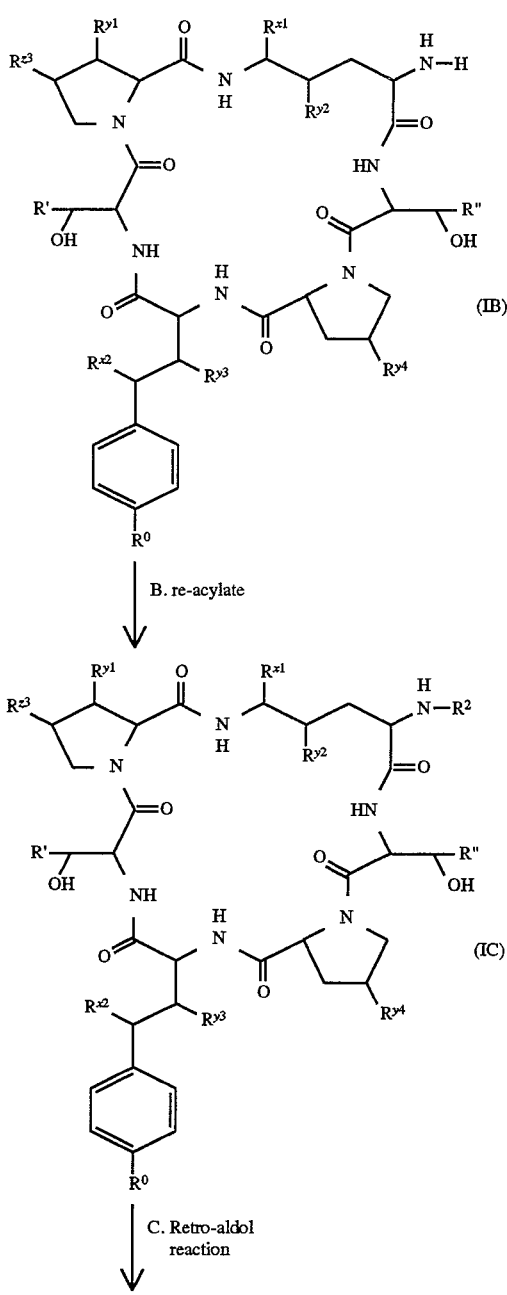

-continued
Reaction Scheme I

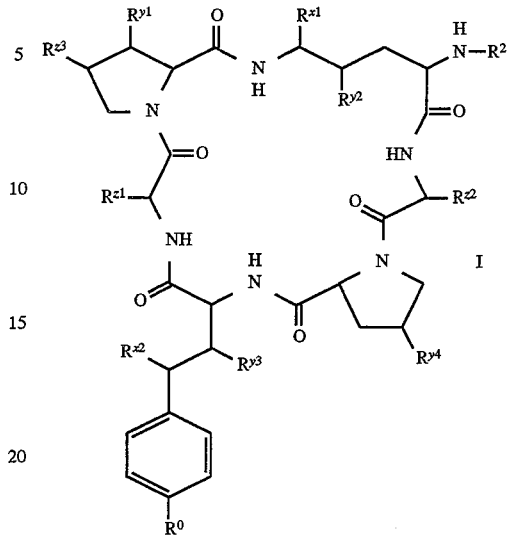

wherein:
$R^{nat}$ is a naturally occurring cyclic peptide sidechain;
R' is hydrogen, methyl or —$CH_2C(O)NH_2$;
R" is hydrogen or methyl; and
$R^{z1}$, $R^{z2}$, $R^{z3}$, $R^{x1}$, $R^{x1'}$, $R^{x2}$, $R^{y1}$, $R^{y2}$, $R^{y3}$, $R^{y4}$, $R^0$ and $R^2$ are as defined above.

Reaction scheme I, above, is accomplished by carrying out reactions A–C, above. Once a reaction is complete, the intermediate compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization or precipitation or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304, 716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), FR901379 (palmitoyl side chain) and the like. A preferred naturally occurring cyclic peptide is echinocandin B (a compound of formula IA where R', R" and $R^{z3}$ are each methyl, $R^{x1}$, $R^{x2}$, $R^{y1}$, $R^{y2}$, $R^{y3}$, $R^{y4}$ and $R^o$ are each hydroxy and $R^2$ is linoleoyl).

In Reaction IB, the amino nucleus of formula IB is re-acylated using procedures known in the art to provide a compound of formula IC where $R^2$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about $-20°$ C. to about $25°$ C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOPCl), N-ethoxycarbonyl-2-ethoxy-1,2-dihydroquinoline (EEDQ), benzotriazol-1-yloxytripyrrolidinophosphonium hexafluorophosphate (PyBOP) and the like.

In addition, the amino nucleus may be acylated with an activated ester of a carboxylic acid such as an ester of a carboxylic acid of the formula $R^2$—COOH and p-nitrophenyl, 2,4,5-trichlorophenyl, hydroxybenzotriazole hydrate (HOBT.H$_2$O), pentafluorophenol, N-hydroxysuccinimide and the like. Preferred acylating moieties are the active esters of the carboxylic acid $R^2$—COOH such as 2,4,5-trichlorophenyl ester and benzotriazole ester. The reaction is typically carried out for one to sixty five hours at a temperature from about $0°$ C. to about $30°$ C. in an aprotic solvent. The reaction is generally complete after about twenty four to forty eight hours when carried out a temperature of from about $15°$ C. to about $30°$ C. Typical solvents for this reaction are tetrahydrofuran and dimethylformamide or a mixture of such solvents. The amino nucleus is generally employed in equimolar proportions relative to the activated ester or with a slight excess of the amino nucleus.

In Reaction IC, one or both of the β-hydroxy groups are selectively removed from a compound of formula IC to provide a compound of formula I. Specifically, the compound of formula IC is heated in an aprotic solvent to between about $50°$ C. and $100°$ C. in the presence of at least about five equivalents (preferably at least ten equivalents) of a retro-aldol-promoting reagent selected from the group consisting of trimethylamine-N-oxide, triethylamine-N-oxide, trimethylamine-N-oxide-hydrate and trimethylamine-N-oxide-hydrate. The reaction is generally conducted in a sealed tube or in a round bottom flask supplied with a water condenser for approximately three to seventy two hours. The reaction is preferably conducted at a temperature of about $70°$ C. to about $100°$ C., preferably at about $70°$ C. Typical aprotic solvents include dimethylformamide, tetrahydrofuran, acetonitrile, dimethylsulfoxide and the like. A preferred solvent is acetonitrile. Preferred retro-aldol-promoting reagents are trimethylamine-N-oxide and trimethylamine-N-oxide-hydrate. The most preferred retro-aldol-promoting reagent is trimethylamine-N-oxide-hydrate. This reaction is preferably conducted after protecting the aminal hydroxy ($R^{x1}$) of the compound of formula IC. The hydroxy protecting group may be removed after removal of the β-hydroxy group(s), using procedures known in the art.

The term "aldol" indicates a molecule that is both an alcohol and an aldehyde or ketone wherein the hydroxyl and carbonyl functional groups are on adjacent carbon atoms as shown below. Thus, as used herein, the term "β-hydroxy group" refers to the alcohol moiety including both the β-carbon and the hydroxyl functional group that is resident on the β-carbon according to the following general structure:

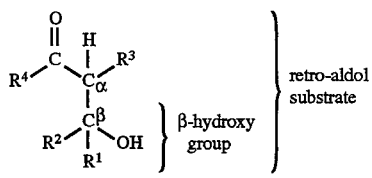

where:

$R^1$ and $R^2$ are independently hydrogen or methyl;

$R^3$ and $R^4$ taken together with the atoms to which they are attached form a cyclic peptide.

The compounds where $R^{x1}$ is —O—$R^{x1'}$ may be prepared by the corresponding compound where $R^{x1}$ is hydroxy with an appropriately substituted alcohol in the presence of an acid to provide a compound of formula I wherein $R^{x1}$ is —O—$R^{x1'}$ where $R^{x1'}$ is $C_1$-$C_6$ alkyl, benzyl, —(CH$_2$)$_2$Si(CH$_3$)$_3$, —CH$_2$CH=CH$_2$, —(CH$_2$)$_a$COOH, —(CH$_2$)$_b$NR$^{w1}$R$^{w2}$, —(CH$_2$)$_c$POR$^{w3}$R$^{w4}$ or —[(CH$_2$)$_2$O]$_d$—(C$_1$-C$_6$)alkyl. The compounds where $R^{x1}$ is —O—$R^{x1'}$ are preferably prepared after removal of the β-hydroxy group(s) The reaction is typically carried out in a polar aprotic solvent such as dioxane or dimethylsulfoxide at a temperature of from about $0°$ C. to about $35°$ C., preferably at about room temperature. Solvent choice is not critical so long as the solvent employed is inert to the ongoing reaction and the reactants are sufficiently solubilized to effect the desired reaction. Preferred acids include p-toluenesulfonic acid hydrochloric acid and camphorsulfonic acid The compounds where $R^{x1'}$ is —(CH$_2$)$_b$NR$^{w1}$R$^{w2}$ where $R^{w1}$ and $R^{w2}$ are hydrogen may be prepared via a protected compound wherein $R^{x1}$ is —(CH$_2$)$_b$NHR$^a$ where $R^a$ is an amino protecting group. The resultant protected compound may be deprotected according to procedures known in the art.

The compounds where $R^{x1'}$ is —CH$_2$CHOHCH$_2$OH may be prepared by hydroxylating a compound of formula I where $R^{x1'}$ is —CH$_2$CH=CH$_2$ with osmium tetroxide in the presence of a catalyst at a temperature in the range of from about $0°$ C. to about $40°$ C. for about one to twenty four hours in a organic/aqueous solvent mixture for example dioxane/water. Suitable catalysts include N-methylmorpholine N-oxide (NMO) and the like. Typical solvents suitable for use in this reaction include dimethylformamide, tetrahydrofuran, ethyl acetate, dioxane or a mixture of these solvents. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about eighteen to twenty four hours.

The compounds where $R^o$ is hydroxy may be phosphorylated by reaction with an appropriately substituted alkyl, phenyl or benzyl phosphate to provide a compound where $R^o$ is —O—P(O)OH—OR$^1$ where R$^1$ is C$_1$-C$_6$ alkyl, phenyl or benzyl, or by reaction with an appropriately substituted alkyl, phenyl or benzyl phosphonic acid to provide a compound where $R^o$ is —OP(O)OH—R$^1$ where R$^1$ is C$_1$-C$_6$ alkyl, phenyl or benzyl, to provide a compound of formula I where $R^o$ is a group of the formula —OP(O)OH—OR$^1$ or —OP(O)OH—R$^1$. This reaction is preferably conducted after removal of the β-hydroxy group(s). The phosphonic acid is typically used in an activated form, for example as a phosphonic halide, preferably a phosphonic chloride. The reaction is carried out in the presence of a base such as lithium trimethylsilanolate (LiOTMS), lithium bis (trimethylsilyl)amide (LHMDS), pyridine and the like. The reaction is typically carried out for up to one hour at a temperature from about −30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups is typically carried out at lower temperatures, for example from about −30° C. to about −15° C.

Alternatively, the compounds where $R^{x1}$ is hydroxy may be phosphorylated after first protecting the hydroxy moiety with an hydroxy protecting group using procedures known in the art. For example, the reaction is typically carried out by combining the compound with a suitable hydroxy protecting group in the presence of a catalyst at a temperature in the range of from about 0° C. to about 40° C. for about one to five hours in a mutual inert solvent. The hydroxy protecting group is generally employed in an amount ranging from about equimolar proportions to about a 100 molar excess relative to the compound, preferably in a large molar excess. Suitable catalysts include strong acids such as p-toluenesulfonic acid, camphorsulfonic acid (CSA), hydrochloric acid, sulfuric acid, trifluoroacetic acid and the like. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about two to four hours. The protected compound is then phosphorylated as described above. The hydroxy protecting group is then removed according to procedures known in the art to provide the desired phosphorylated compound. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The dideoxy compounds are prepared by removing the benzylic and aminal hydroxy groups ($R^{x2}$ and $R^{x1}$, respectively). The hydroxy groups may be removed by subjecting a non-dideoxy compound to a strong acid and a reducing agent at a temperature of between −5° C. and 70° C., in a suitable solvent. Typical strong acids include trichloroacetic acid, trifluoroacetic acid or borontrifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 80 mol per mol of substrate, and the reducing agent should be present in an amount of 2 to 80 mol per mol of substrate. This process affords selective removal of the aminal and benzylic hydroxy groups.

The cyclic peptides used to make the compounds of the present invention may be prepared by fermentation of known microorganisms. For example, the cyclic peptide of formula IB where R', R" and $R^{z3}$ are methyl, and $R^{x1}$, $R^{x2}$, $R^{y1}$, $R^{y2}$, $R^{y3}$, $R^{y4}$ and $R^o$ are each hydroxy (cyclic nucleus corresponding to A-30912A) may be prepared using the procedure detailed in Abbott et al., U.S. Pat. No. 4,293,482, which is herein incorporated by reference. The cyclic peptide of formula IB where R', R" and $R^{z3}$ are methyl, $R^{x1}$ is hydroxy, $R^{x2}$ is hydrogen, and $R^{y1}$, $R^{y2}$, $R^{y3}$, $R^{y4}$ and $R^o$ are each hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is —CH$_2$C(O)NH$_2$, R" is methyl, $R^{z3}$ is hydrogen, and $R^{x1}$, $R^{x2}$, $R^{y1}$, $R^{y2}$, $R^{y3}$, $R^{y4}$ and $R^o$ are each hydroxy may be prepared by deacylating the cyclic peptide prepared using the procedure detailed in Chen et al., U.S. Pat. No. 5,198,421, which is herein incorporated by reference.

The R$^2$—COOH precursor acids, used to acylate the amino nucleus of formula IB, may be obtained commercially or prepared according to procedures known in the art. For example, an appropriately substituted phenyl boronic acid or biphenyl boronic acid reactant may be reacted with a p-halobenzoic acid reactant in the presence of a catalyst such as tetrakis(triphenylphosphine)palladium and an inorganic base such as potassium carbonate in a mutual inert organic solvent such as toluene at a temperature of from about 20° C. to the reflux temperature of the reaction mixture to provide the corresponding biphenyl carboxylic acids and terphenyl carboxylic acids used to prepare the compounds of formula I. The reaction is typically carried out with equimolar proportions of the boronic acid reactant and the p-benzoic acid reactant, or a slight molar excess of the p-benzoic acid reactant relative to the boronic acid reactant, and a 1–2 molar excess of the inorganic base. The reaction is generally complete after about four to about ten hours when carried out at reflux temperature in toluene.

The boronic acid reactant may be prepared by reacting an appropriately substituted halophenyl or halobiphenyl reactant with two equivalents of triisopropyl borate in the presence of an alkyl lithium, for example sec-butyl lithium, in a mutual inert solvent such as tetrahydrofuran. The alkyl lithium is typically employed in a slight molar excess relative to the halophenyl or halobiphenyl reactant. The alkyl lithium is typically combined with the solvent by dropwise addition at reduced temperatures (<−70° C.) and allowed to stir for approximately thirty minutes before the addition of the triisopropyl borate. The reaction is typically carried out initially at a temperature of from about −100° C. to about −50° C., preferably from about −75° C. to about −85° C. for thirty minutes to two hours and then warmed to room temperature and reacted for an additional one to three hours. The reaction is generally complete in from several minutes to about four hours. When the reaction is substantially complete, the boronic acid moiety is formed by the addition of an acid. A preferred acid is a 1N hydrochloric acid solution.

The carboxylic acids, $R^2$—COOH, having an acetylene moiety may be prepared by reacting an appropriately substituted acetylene reactant with an appropriately substituted phenyl or biphenyl reactant of the formula

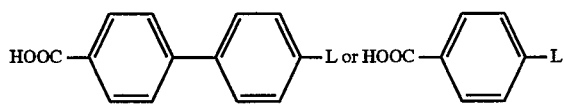

where L is a suitable leaving group such as bromo, iodo, methanesulfonate, toluenesulfonate, trifluoromethanesulfonate and the like, in the presence of a catalyst and preferably in the presence of an acid scavenger in a mutual inert solvent such as acetonitrile. Examples of acid scavengers include triethylamine and pyridine, preferably triethylamine. A preferred catalyst is formed in situ from palladium (II) chloride, triphenylphosphine and copper (I) iodide. The reaction is typically carried out for thirty minutes to twenty one hours at a temperature from about room temperature to the reflux temperature of reaction mixture. The reaction is generally complete after about two to about six hours when carried out at reflux temperature.

Alternatively, a suitably substituted phenyl reactant of the formula

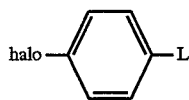

may be reacted with an appropriately substituted acetylene reactant as described above to provide, for example, a compound of the formula

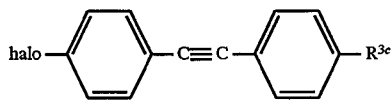

which can be coupled with a phenyl boronic acid reactant as described above.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

EXAMPLE 1

A. Preparation of the compound of formula IC where R', R" and $R^{z3}$ are each methyl, $R^{x1}$ and $R^{x2}$ are each hydroxy, $R^{y1}$, $R^{y2}$, $R^{y3}$ and $R^{y4}$ are each hydroxy, $R^o$ is hydroxy and $R^2$ is

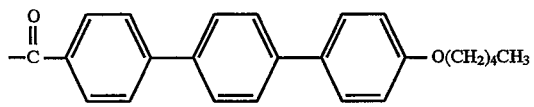

The N-acyl cyclic peptide derivatives listed in Table 3, below were prepared by dissolving 348.1 g (60.2 mmol) of the A30912A nucleus (compound of formula IB where R', R" and $R^{z3}$ are each methyl, $R^{x1}$ and $R^{x2}$ are each hydroxy, $R^{y1}$, $R^{y2}$, $R^{y3}$ and $R^{y4}$ are each hydroxy, and $R^o$ is hydroxy) and 26.0 g (48.2 mmol) of the 2,4,5-trichlorophenol ester of [(4"-pentyloxy)-1,1':4',1"-terphenyl]-4-carboxylic acid, in 8.5 l of dimethylformamide. The resultant reaction mixture was stirred for approximately 48 hours at room temperature and then the solvent was removed in vacuo to provide a residue. This residue was slurried in ether, collected by filtration, washed with methylene chloride and then dissolved in methanol or a 1:1 (v/v) acetonitrile/water mixture. The resultant solution is subjected to reverse phase HPLC (C18; eluent of 20–40% aqueous acetonitrile containing 0.5% monobasic ammonium phosphate (w/v); 20 ml/min.; 230 nm). After removing the unreacted A30912A nucleus, the desired product was eluted from the column using an eluent of aqueous acetonitrile. The fractions containing the desired product are combined and then reduced to dryness in vacuo to provide the desired acylated nucleus.

Yield: 18 g. MS(FAB): 1140.5103 (M+$^1$).

B. Preparation of the compound of formula IC where R', R" and $R^{z3}$ are each methyl, $R^{x1}$ and $R^{x2}$ are each hydrogen, $R^{y1}$, $R^{y2}$, $R^{y3}$ and $R^{y4}$ are each hydroxy, $R^o$ is hydroxy and $R^2$ is

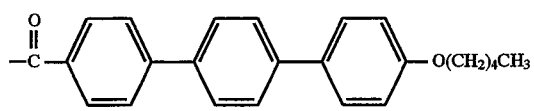

To a mixture of 5 g (4.4 mmol) of the compound prepared in Example 1A and 17 ml of trifluoroacetic acid in 250 ml of methylene chloride, was added 35 ml of triethylsilane. When the reaction was substantially complete, as indicated by HPLC (C18, eluent of 55% acetonitrile; 2 ml/min; 280 nm; $R_T$ (starting material) =4.19 min.; $R_T$ (product)=6.40 min.), the reaction mixture was concentrated in vacuo to provide a solid. This solid was slurried in 100 ml of 50% aqueous acetone and then dissolved by adjusting the pH of the mixture to approximately pH 7. The resultant solution was poured into a large volume of water (approximately 1 liter) resulting in the precipitation of a white solid. This solid was isolated by filtration through a sintered glass funnel, washed with diethyl ether and then dried in vacuo at 55° C. to provide 3.718 g of the titled compound. The funnel was washed with methanol to collect the remaining solid, which was dried in vacuo to provide an additional 0.154 g of the titled compound.

Yield: 3.872 g (79%). MS (FAB): m/e 1108.7 (M) HPLC: (eluent of 55% acetonitrile; 2 ml/min.; 280 nm): $R_T$=6.43 min.

C. Preparation of the compound of formula I where $R^{z1}$ and $R^{z2}$ are each hydrogen, $R^{z3}$ is methyl, $R^{x1}$ and $R^{x2}$ are each hydrogen, $R^{y1}$, $R^{y2}$, $R^{y3}$ and $R^{y4}$ are each hydroxy, $R^o$ is hydroxy and $R^2$ is

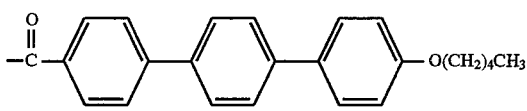

The compound prepared in Example 1B was dissolved in a 1:1 mixture of acetonitrile and dimethylformamide. To this solution, was added TNO-hydrate (1.6 g, 14.3 mmol) all at once. The reaction mixture was heated at 100° C. for 48 hours after which the mixture was cooled to room temperature and concentrated to approximately one-half its original volume. The crude residue was dissolved with acetic acid and purified by reverse phase preparative HPLC to yield 150 mg final product (52%). TNO-hydrate converted the two threonine residues into glycine residues and left the homotyrosine untouched as confirmed by fast atom bombardment mass spectrometry, which confirmed the molecular weight of the product having the chemical formula $C_{54}H_{65}N_7O_{13}$:

calculated—1020.1; found—1020.8. (M+H).

EXAMPLE 2

Alternative Preparation of the compound of formula I where $R^{z1}$ and $R^{z2}$ are each hydrogen, $R^{z3}$ is methyl, $R^{x1}$ and $R^{x2}$ are each hydrogen, $R^{y1}$, $R^{y2}$, $R^{y3}$ and $R^{y4}$ are each hydroxy, $R^o$ hydroxy and $R^2$ is

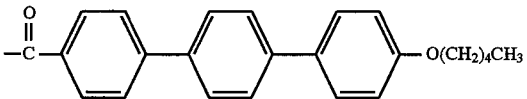

The compound prepared in Example 1B was dissolved in 20 ml of a 1:1 mixture of acetonitrile and dimethylformamide. To this solution, was added trimethylamine N-oxide dihydrate (2.51 g, 22.6 mmol) all at once. The reaction mixture was heated at 100° C. for 24 hours in a sealed tube after which the mixture was cooled to room temperature and concentrated in vacuo to approximately one-half its original volume. The crude residue was isolated by filtration and then rinsed with cold dimethylformamide. The resultant filtrate was dried in vacuo to provide a residue. This residue was purified using reverse phase HPLC (3×40×10 radial column, eluent of 50% acetonitrile in water, 60 ml/min., 280 nm) to yield 330 mg final product (72%). Fast atom bombardment mass spectrometry confirmed the molecular weight of the product having the chemical formula $C_{54}H_{65}N_7O_{13}$:

calculated—1020.1; found—1020.4 (M+H).

The compounds of formula I exhibit antifungal activity. For example, the compounds of formula I inhibit the growth of various infectious fungi including *Candida spp.* such as *C. albicans, C. parapsilosis, C. krusei, C. glabrata,* or *C. tropicalis, C. lusitaniae; Torulopus spp.* such as *T. glabrata; Aspergillus spp.* such as *A. fumigatus; Histoplasma spp.* such as *H. capsulatum; Cryptococcus spp.* such as *C. neoformans; Blastomyces spp.* such as *B. dermatitidis; Fusarium spp., Trichophyton spp., Pseudallescheria boydii, Coccidioides immi tis, Sporothrix schenckii* and the like.

Antifungal activity of a test compound is determined in vitro by obtaining the minimum inhibitory concentration (MIC) of the compound using a standard agar dilution test or a disc-diffusion test. The compound is then tested in vivo (in mice) to determine the effective dose of the test compound for controlling a systemic fungal infection.

Accordingly, the compound prepared in Example 1C was tested for antifungal activity against *C. albicans*. The minimal inhibitory concentration (MIC) of this compound against *C. albicans* was 0.312 (μg/ml).

In addition, the effective dose of the compound prepared in Example 1C, for controlling a systemic fungel infection (*C. albicans*), was tested in vivo (mice). The $ED_{50}$ for this compound was >2.5.

The compounds of formula I are active in vitro and in vivo and are useful in combating either systemic fungel infections or fungel skin infections. Accordingly, the present invention provides a method of inhibiting fungel activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

We claim:

1. A compound of formula I:

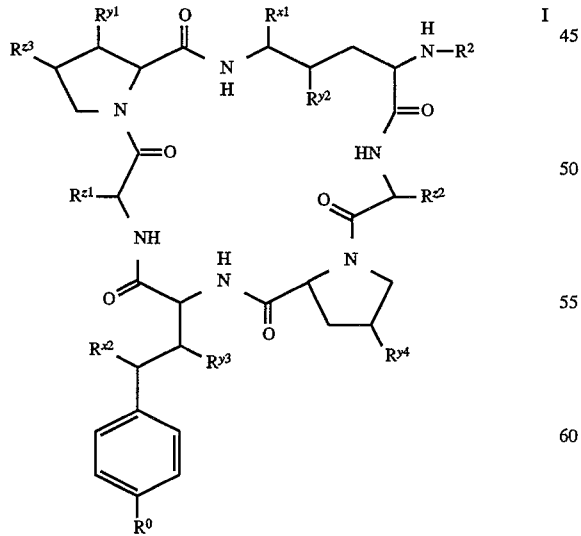

wherein:

$R^{z1}$ is hydrogen, —$CH_2OH$, —$CHOHCH_3$ or —$CHOHCH_2C(O)NH2$;

$R^{z2}$ is hydrogen, —$CH_2OH$ or —$CHOHCH_3$;

$R^{z3}$ is hydrogen or methyl;

$R^{x1}$ is hydrogen, hydroxy or O—$R^{x1'}$;

$R^{x1'}$ is $C_1$-$C_6$ alkyl, benzyl, —$(CH_2)_2Si(CH_3)_3$, —$CH_2CH$=$CH_2$, —$CH_2CHOHCH_2OH$, —$(CH_2)_aCOOH$, —$(CH_2)_bNR^{w1}R^{w2}$, —$(CH_2)_cPOR^{w3}R^{w4}$ or —$[(CH_2)_2O]_d$—$(C_1$-$C_6)$alkyl;

a, b and c are independently 1, 2, 3, 4, 5 or 6;

$R^{w1}$ and $R^{w2}$ are independently hydrogen, $C_1$-$C_6$ alkyl, or $R^{w1}$ and $R^{w2}$ combine to form —$CH_2(CH_2)_eCH_2$—;

$R^{w3}$ and $R^{w4}$ are independently hydroxy, or $C_1$-$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen $R^0$ is hydroxy, —$OP(O)(OH)_2$ or a group of the formulae:

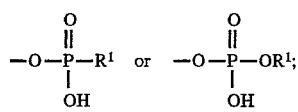

$R^1$ is $C_1$-$C_6$ alkyl, phenyl, p-halo-phenyl, p-nitrophenyl, benzyl, p-halo-benzyl or p-nitro-benzyl;

$R^2$ is

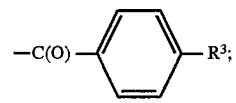

$R^3$ is

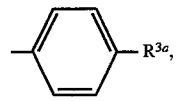

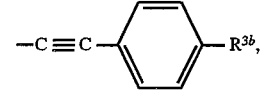

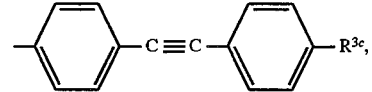

or

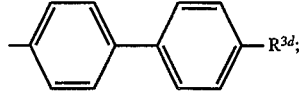

$R^{3a}$, $R^{3b}$, $R^{3c}$ and $R^{3d}$ are independently hydrogen, $C_1$-$C_{12}$ alkyl, $C_2$-$C_{12}$ alkynyl, $C_1$-$C_{12}$ alkoxy, $C_1$-$C_{12}$ alkylthio, halo, —O—$(CH_2)_m$—[O—$(CH_2)_n]_p$—O—($C_1$-$C_{12}$ alkyl) or —O—$(CH_2)_q$—X—$R^4$;

m is 2, 3 or 4;

n is 2, 3 or 4;

p is 0 or 1;

q is 2, 3 or 4;

X is pyrrolidino, piperidino or piperazino; and $R^4$ is hydrogen, $C_1$-$C_{12}$ alkyl, $C_3$-$C_{12}$ cycloalkyl, benzyl or $C_3$-$C_{12}$ cycloalkylmethyl;

with the proviso that at least one of $R^{z1}$ and $R^{z2}$ must be hydrogen;
or a pharmaceutically acceptable salt thereof.

2. A compound according to claim 1 where:
$R^{z1}$ is hydrogen, —CH$_2$OH or —CHOHCH$_3$; or a pharmaceutically acceptable salt thereof.

3. A compound according to claim 2 where:
$R^{z1}$ and $R^{z2}$ are independently hydrogen or —CHOHCH$_3$;
$R^{z3}$ is methyl;
$R^{y1}$, $R^{y2}$, $R^{y3}$ and $R^{y4}$ are each hydroxy;
$R^{x1}$ is hydrogen, hydroxy or —OR$^{x1'}$;
$R^{x1'}$ is methyl, benzyl, —CH$_2$CHOHCH$_2$OH, —CH$_2$COOH, —(CH$_2$)$_2$NR$^{w1}$R$^{w2}$ or —(CH$_2$)$_2$POR$^{w3}$R$^{w4}$;
$R^{w1}$ and $R^{w2}$ are independently hydrogen or methyl;
$R^{w3}$ and $R^{w4}$ are independently hydrogen or methoxy;
$R^0$ is hydroxy or a group of the formulae:

$$-O-\underset{\underset{OH}{|}}{\overset{\overset{O}{\|}}{P}}-R^1 \quad \text{or} \quad -O-\underset{\underset{OH}{|}}{\overset{\overset{O}{\|}}{P}}-OR^1;$$

$R^1$ is methyl;
or a pharmaceutically acceptable salt thereof.

4. A compound according to claim 3 where:
$R^{z1}$ and $R^{z2}$ are both hydrogen;
$R^{x1}$ is hydrogen;
$R^{x2}$ is hydrogen;
$R^3$ is

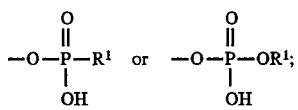

or

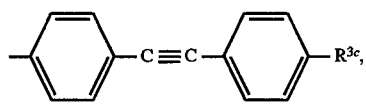

$R^{3c}$ and $R^{3d}$ are independently hydrogen, C$_1$-C$_{12}$ alkyl, C$_2$-C$_{12}$ alkynyl, C$_1$-C$_{12}$ alkoxy or —O—(CH$_2$)$_2$—O—(C$_1$-C$_{12}$ alkyl);
or a pharmaceutically acceptable salt thereof.

5. A compound according to claim 4 where:
$R^3$ is

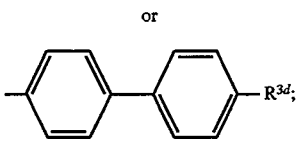, or

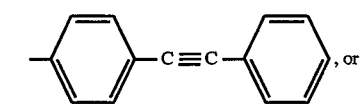

or a pharmaceutically acceptable salt thereof.

6. A pharmaceutical formulation comprising one or more pharmaceutically acceptable carriers, diluents or excipients and a compound of claim 1.

7. A pharmaceutical formulation according to claim 6 where the compound is one wherein:

$R^{z1}$ is hydrogen, —CH$_2$OH or —CHOHCH$_3$;
or a pharmaceutically acceptable salt thereof.

8. A pharmaceutical formulation according to claim 7 where the compound is one wherein:
$R^{z1}$ and $R^{z2}$ are independently hydrogen or —CHOHCH$_3$;
$R^{z3}$ is methyl;
$R^{y1}$, $R^{y2}$, $R^{y3}$ and $R^{y4}$ are each hydroxy;
$R^{x1}$ is hydrogen, hydroxy or —OR$^{x1'}$;
$R^{x1'}$ is methyl, benzyl, —CH$_2$CHOHCH$_2$OH, —CH$_2$COOH, —(CH$_2$)$_2$NR$^{w1}$R$^{w2}$ or —(CH$_2$)$_2$POR$^{w3}$R$^{w4}$;
$R^{w1}$ and $R^{w2}$ are independently hydrogen or methyl;
$R^{w3}$ and $R^{w4}$ are independently hydrogen or methoxy;
$R^0$ is hydroxy or a group of the formulae:

$$-O-\underset{\underset{OH}{|}}{\overset{\overset{O}{\|}}{P}}-R^1 \quad \text{or} \quad -O-\underset{\underset{OH}{|}}{\overset{\overset{O}{\|}}{P}}-OR^1;$$

$R^1$ is methyl;
or a pharmaceutically acceptable salt thereof.

9. A pharmaceutical formulation according to claim 8 where the compound is one wherein:
$R^{z1}$ and $R^{z2}$ are both hydrogen;
$R^{x1}$ is hydrogen;
$R^{x2}$ is hydrogen;
$R^3$ is

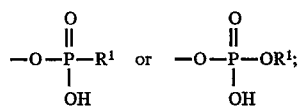

or

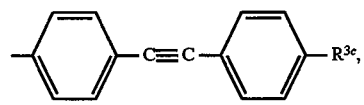

$R^{3c}$ and $R^{3d}$ are independently hydrogen, C$_1$-C$_{12}$ alkyl, C$_2$-C$_{12}$ alkynyl, C$_1$-C$_{12}$ alkoxy or —O—(CH$_2$)$_2$—O—(C$_1$-C$_{12}$ alkyl);
or a pharmaceutically acceptable salt thereof.

10. A pharmaceutical formulation according to claim 9 where the compound is one wherein:
$R^3$ is

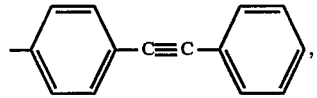, or

or a pharmaceutically acceptable salt thereof.

11. A method of inhibiting fungal activity comprising contacting a compound of claim 1 with a fungus.

12. A method according to claim 11 where the compound is one wherein:
$R^{z1}$ is hydrogen, —CH$_2$OH or —CHOHCH$_3$;

or a pharmaceutically acceptable salt thereof.

13. A method according to claim 12 where the compound is one wherein:

$R^{z1}$ and $R^{z2}$ are independently hydrogen or —CHOHCH$_3$;
$R^{z3}$ is methyl;
$R^{y1}$, $R^{y2}$, $R^{y3}$ and $R^{y4}$ are each hydroxy;
$R^{x1}$ is hydrogen, hydroxy or —OR$^{x1'}$;
$R^{x1'}$ is methyl, benzyl, —CH$_2$CHOHCH$_2$OH, —CH$_2$COOH, —(CH$_2$)2NR$^{w1}$R$^{w2}$ or —(CH$_2$)$_2$POR$^{w3}$R$^{w4}$;
$R^{w1}$ and $R^{w2}$ are independently hydrogen or methyl;
$R^{w3}$ and $R^{w4}$ are independently hydrogen or methoxy;
$R^0$ is hydroxy or a group of the formulae:

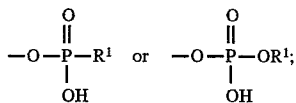

$R^1$ is methyl;
or a pharmaceutically acceptable salt thereof.

14. A method according to claim 13 where the compound is one wherein:

$R^{z1}$ and $R^{z2}$ are both hydrogen;
$R^{x1}$ is hydrogen;
$R^{x2}$ is hydrogen;
$R^3$ is

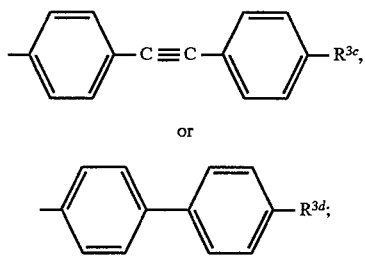

$R^{3c}$ and $R^{3d}$ are independently hydrogen, $C_1$-$C_{12}$ alkyl, $C_2$-$C_{12}$ alkynyl, $C_1$-$C_{12}$ alkoxy or —O—(CH$_2$)$_2$—O—(C$_1$-C$_{12}$ alkyl);
or a pharmaceutically acceptable salt thereof.

15. A method according to claim 14 where the compound is one wherein:

$R^3$ is

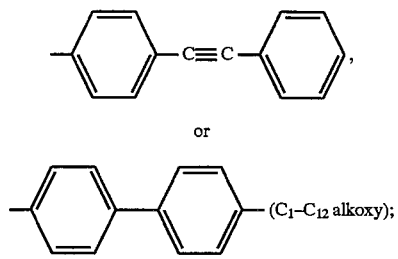

or a pharmaceutically acceptable salt thereof.

16. A method according to claim 15 where the fungus is *Candida albicans*.

17. A method according to claim 15 where the fungus is *Aspergillus fumigatus*.

18. A method of treating a fungal infection which comprises administering an effective amount of a compound of claim 1 to a host in need of such treatment.

19. A method according to claim 18 where the compound is one wherein:

$R^{z1}$ is hydrogen, —CH$_2$OH or —CHOHCH$_3$; or a pharmaceutically acceptable salt thereof.

20. A method according to claim 19 where the compound is one wherein:

$R^{z1}$ and $R^{z2}$ are independently hydrogen or —CHOHCH$_3$;
$R^{z3}$ is methyl;
$R^{y1}$, $R^{y2}$, $R^{y3}$ and $R^{y4}$ are each hydroxy;
$R^{x1}$ is hydrogen, hydroxy or —OR$^{x1'}$;
$R^{x1'}$ is methyl, benzyl, —CH$_2$CHOHCH$_2$OH, —CH$_2$COOH, —(CH$_2$)$_2$NR$^{w1}$R$^{w2}$ or —(CH$_2$)$_2$POR$^{w3}$R$^{w4}$;
$R^{w1}$ and $R^{w2}$ are independently hydrogen or methyl;
$R^{w3}$ and $R^{w4}$ are independently hydrogen or methoxy;
$R^0$ is hydroxy or a group of the formulae:

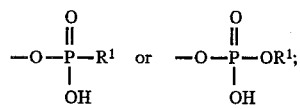

$R^1$ is methyl;
or a pharmaceutically acceptable salt thereof.

21. A method according to claim 20 where the compound is one wherein:

$R^{z1}$ and $R^{z2}$ are both hydrogen;
$R^{x1}$ is hydrogen;
$R^{x2}$ is hydrogen;
$R^3$ is

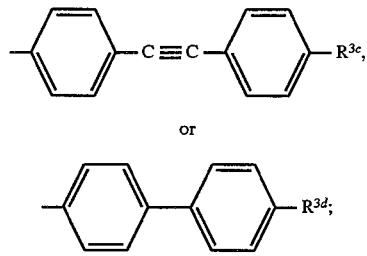

$R^{3c}$ and $R^{3d}$ are independently hydrogen, $C_1$-$C_{12}$ alkyl, $C_2$-$C_{12}$ alkynyl, $C_1$-$C_{12}$ alkoxy or —O—(CH$_2$)$_2$—O—(C$_1$-C$_{12}$ alkyl);
or a pharmaceutically acceptable salt thereof.

22. A method according to claim 21 where the compound is one wherein:

$R^3$ is

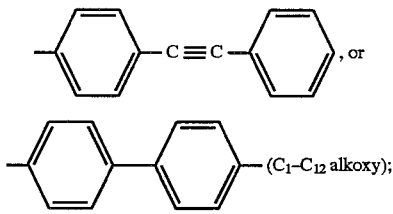

or a pharmaceutically acceptable salt thereof.

23. A method according to claim 22 where the fungal infection is *Candida albicans*.

24. A method according to claim 22 where the fungal infection is *Aspergillus fumigatus*.

* * * * *

UNITED STATES PATENT AND TRADEMARK OFFICE
CERTIFICATE OF CORRECTION

PATENT NO. : 5,629,289
DATED : May 13, 1997
INVENTOR(S) : Michael J. Rodriguez

It is certified that error appears in the above-identified patent and that said Letters Patent is hereby corrected as shown below:

In column 2, line 2, following "is", delete "$C_1-C_6$" and insert --$C_1-C_6$-- therefor.

In column 2, line 4, delete "$R^2$" and insert --$R^{w2}$-- therefor.

In column 15, line 26, following "$R^o$", insert --is--.

In column 15, line 59, following "*Coccidioides*", delete "*immi tis*" and insert --*immitis*-- therefor.

Signed and Sealed this

Twenty-second Day of June, 1999

Attest:

Q. TODD DICKINSON

*Attesting Officer*     *Acting Commissioner of Patents and Trademarks*